United States Patent [19]
Chen et al.

[11] Patent Number: 5,921,244
[45] Date of Patent: Jul. 13, 1999

[54] INTERNAL MAGNETIC DEVICE TO ENHANCE DRUG THERAPY

[75] Inventors: James C. Chen, Bellevue, Wash.; Brent Wiscombe, Mesa, Ariz.; Brian D. Wilkerson, Issaquah, Wash.; Darrin Huston; David J. Brown, both of Enumclaw, Wash.

[73] Assignee: Light Sciences Limited Partnership, Issaquah, Wash.

[21] Appl. No.: 08/873,212

[22] Filed: Jun. 11, 1997

[51] Int. Cl.⁶ .................................................. A61B 19/00
[52] U.S. Cl. ............................ 128/897; 600/9; 604/891.1
[58] Field of Search ................... 128/897–99; 600/9–15; 604/890.1, 891.1, 20

[56] References Cited

U.S. PATENT DOCUMENTS

| | | | |
|---|---|---|---|
| 4,951,675 | 8/1990 | Groman et al. | 600/12 |
| 5,096,763 | 3/1992 | Ogata et al. | 600/12 |
| 5,128,644 | 7/1992 | Nellessen | 600/12 |
| 5,445,608 | 8/1995 | Chen et al. | 604/20 |
| 5,663,701 | 9/1997 | Kaura | 600/12 |

OTHER PUBLICATIONS

Chignell et al., "Rapid Communication—Magnetic Field Effects on the Photohemolysis of Human Erythrocytes by Ketoprofen and Protoporphyrin IX," *Photochemistry and Photobiology*, vol. 62, No. 1, pp. 205–207, 1995, © 1995 American Society for Photobiology.

Cope, "Evaluation of Compression Cholecystogastric and Cholecystojejunal Anastomoses in Swine after Peroral and Surgical Introduction of Magnets," *Journal of Vascular and Interventional Radiology*, vol. 6, No. 4, Jul.–Aug. 1995, pp. 546–552.

Daskalogiannakis et al., "Canine retraction with rare earth magnets: An investigation into the validity of the constant force hypothesis," *American Journal of Orthodontics and Dentofacial Orthopedics*, vol. 109, No. 5, pp. 489–495.

Lübbe et al., "Clinical Experiences with Magnetic Drug Targeting: A Phase I Study with 4'–Epidoxorubicin in 14 Patients with Advanced Solid Tumors," *Cancer Research*, 56, 4686–4693, Oct. 15, 1996.

*Primary Examiner*—John P. Lacyk
*Attorney, Agent, or Firm*—Ronald M. Anderson

[57] ABSTRACT

A magnet used for concentrating a medical substance carried by a magnetic fluid at an internal treatment site. The magnet is inserted through an opening in a patient's body and advanced to the internal treatment site. Although an electromagnet is used in one alternative embodiment, the magnet is preferably a super neodymium or other rare earth permanent magnet having a high field strength. A probe that includes the magnet is coated with a biologically inert material, such as a TEFLON™ polymer. Alternatively, a plurality of such magnets can be employed. In the preferred embodiment, a magnetic fluid that includes particles coated with a photoreactive agent is injected into the patient's body, preferably, immediately adjacent to or inside the treatment site. The particles in the magnetic fluid are attracted to the magnet at the treatment site, and the concentration of the photoreactive agent absorbed into the tissue around the magnet at the internal treatment site is enhanced. The photoreactive agent is used to provide a photodynamic therapy (PDT) to the treatment site that destroys cells that have absorbed the photoreactive agent when the internal treatment site is illuminated by light of an appropriate waveband. A PDT probe having a light source that emits light of the required waveband is inserted into the patient's body and advanced to the treatment site to effect the PDT. The magnet (or magnets) can also be disposed inside the PDT probe, which then carries the magnet(s) to the internal treatment site.

30 Claims, 9 Drawing Sheets

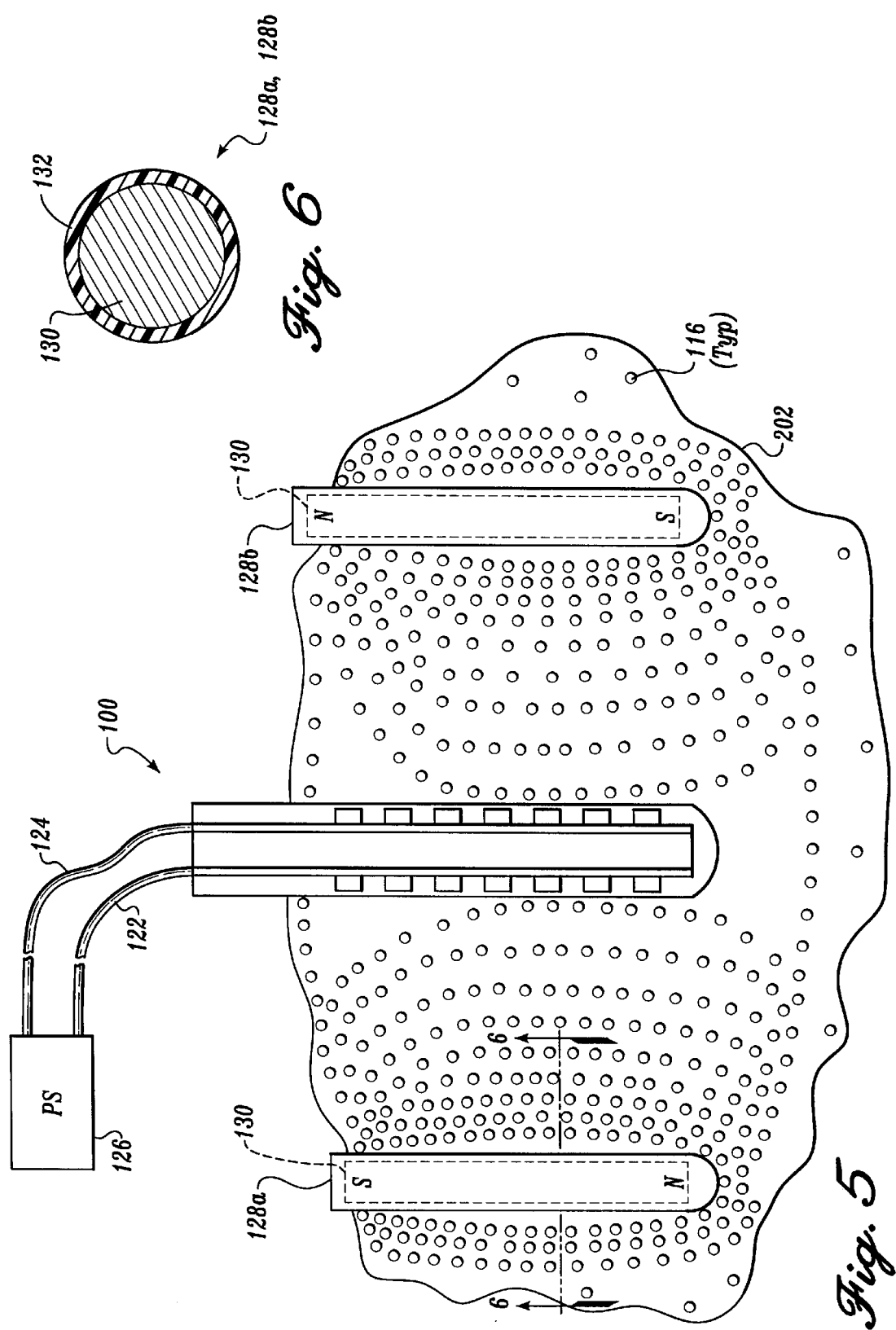

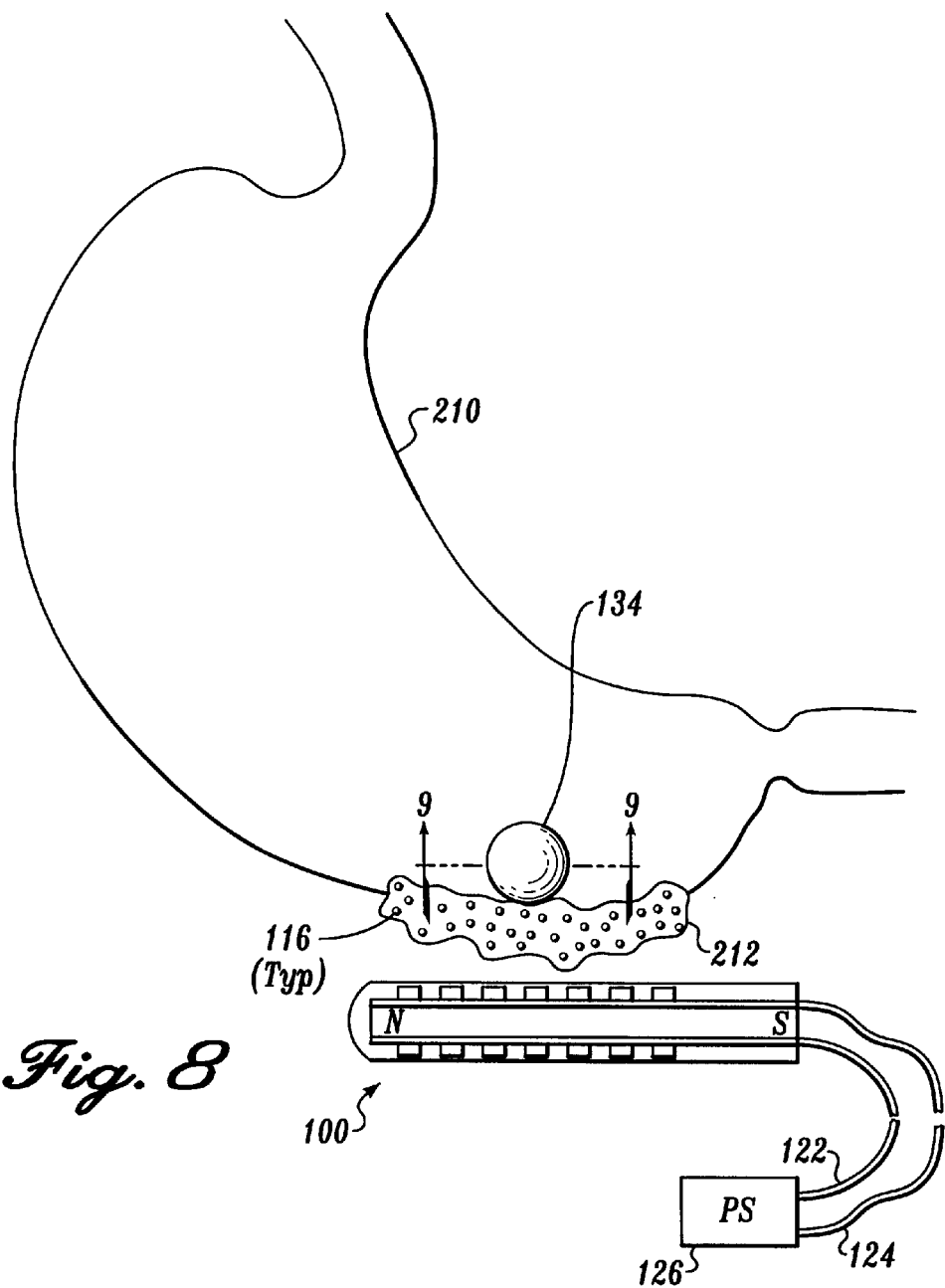

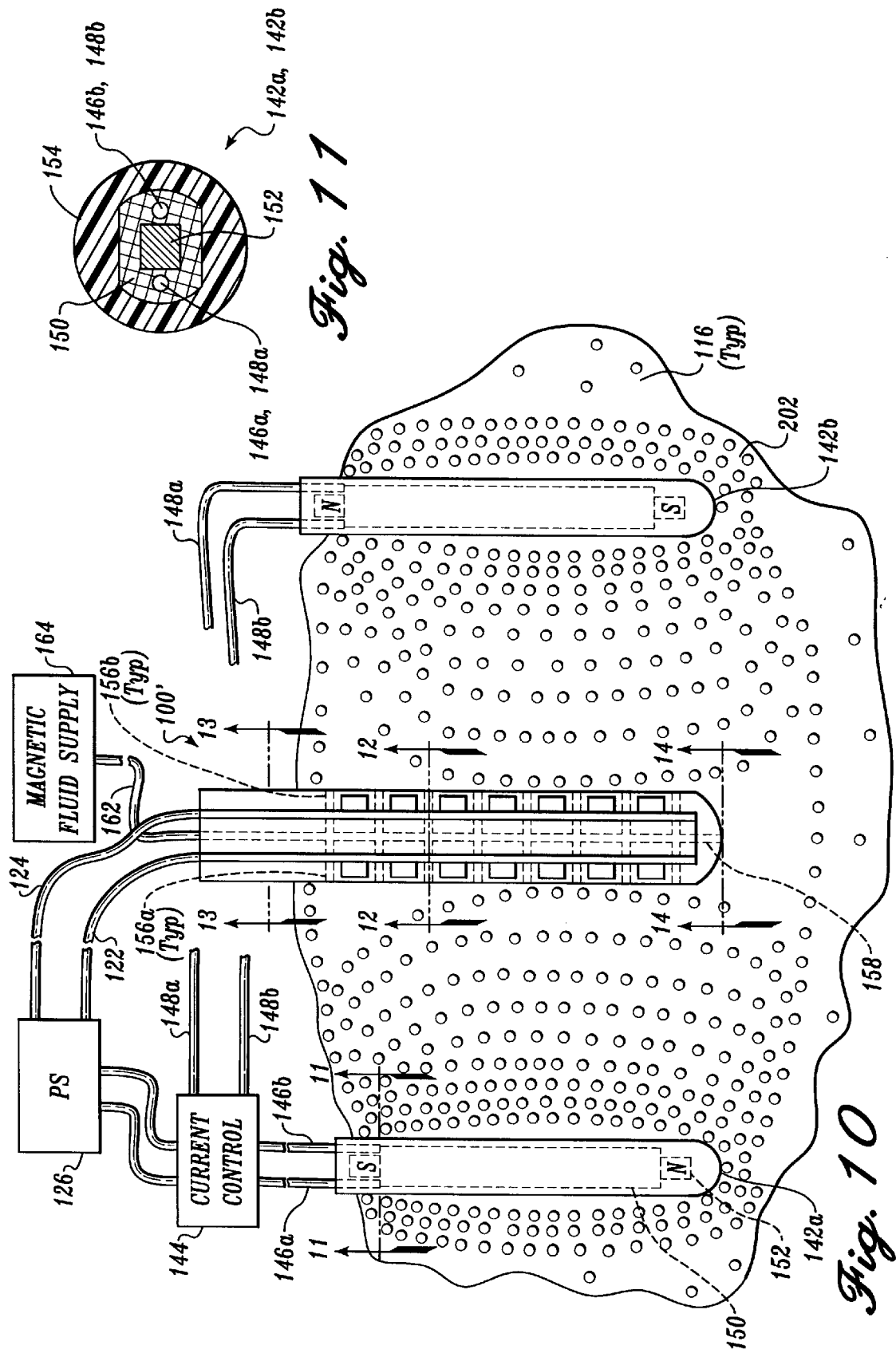

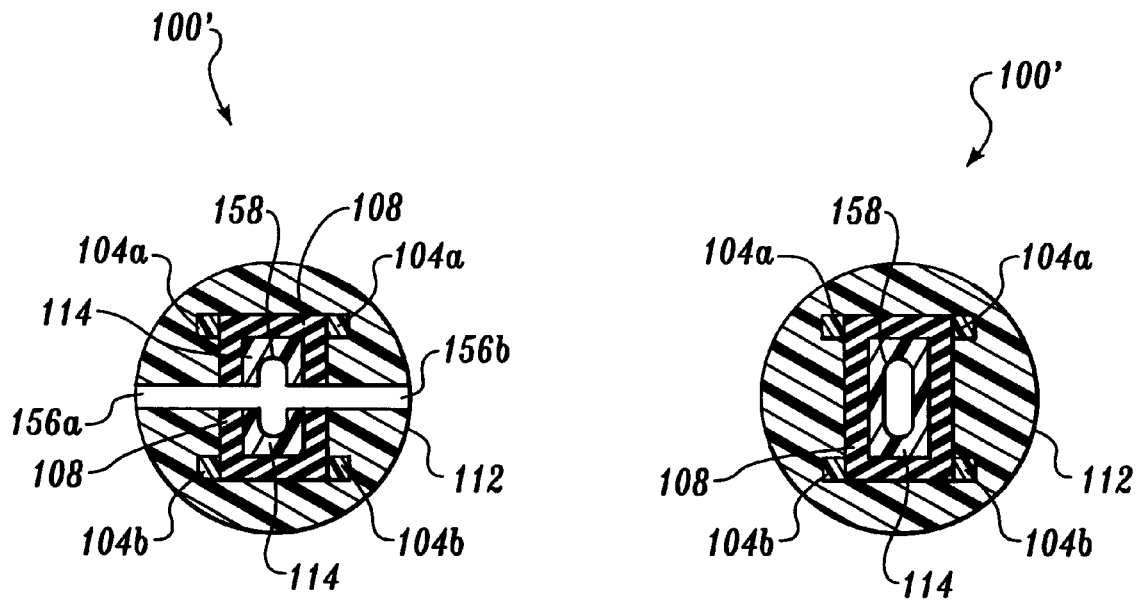
*Fig. 12*  *Fig. 13*
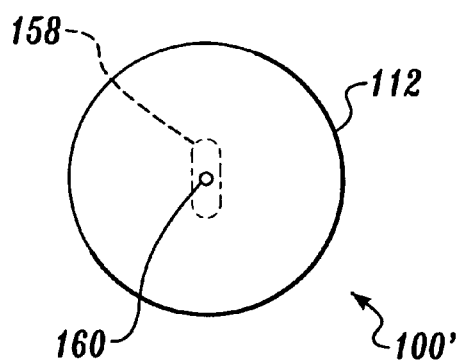
*Fig. 14*

INTERNAL MAGNETIC DEVICE TO ENHANCE DRUG THERAPY

FIELD OF THE INVENTION

The present invention generally relates to an apparatus and a method for concentrating a medicinal substance at an internal treatment site within a patient's body, and more specifically, to an apparatus and a method for attracting a magnetic fluid that includes a medicinal substance to an internal treatment site, using an implanted magnet.

BACKGROUND OF THE INVENTION

Although, in theory, a therapeutic drug is employed to treat only diseased tissue in a patient's body, in practice, conventional drug delivery techniques normally provide the same concentration of the drug in both diseased tissue and healthy tissue throughout the patient's body. Since most conventional techniques do not deliver a drug solely to the diseased tissue, a larger dosage of a particular therapeutic drug must be employed than the dose that would otherwise be required to treat the diseased tissue if the drug were delivered only to the diseased tissue. Further, many therapeutic drugs can adversely affect the healthy tissue of a patient, causing undesired side effects that can even be potentially harmful to healthy tissue. Moreover, the conundrum of causing some harm to healthy tissue, so that diseased tissue can be treated with a therapeutic drug, is particularly acute in therapies employing drugs having low therapeutic indices, such as cytotoxic anticancer drugs. Certain photoreactive drugs, while preferentially absorbed by abnormal tissue, are somewhat toxic to normal tissue. When such drugs are infused into a patient's circulatory system with the intent that they be carried to a treatment site within an organ, the photoreactive agent can adversely impact the normal tissue that they contact, having an undesired affect on the patient's health.

Photoreactive agents are employed when administering photodynamic therapy (PDT). During PDT, light is used to destroy abnormal cells in tumors and pathogenic organisms. Commonly assigned U.S. Pat. No. 5,445,608 discloses several different embodiments for transcutaneously implantable light source probes to administer PDT. Preferably, these probes include a plurality of relatively low intensity light sources, such as light emitting diodes (LEDs). In the above-referenced patent, it is generally contemplated that a probe containing a plurality of light sources is transcutaneously introduced to a desired internal treatment site through a surgical incision and left in place for an extended period of time, so that the light emitted by LEDs or other types of light sources included in the probe can administer PDT to destroy abnormal cells that have absorbed a photoreactive agent. Before administering PDT, the photoreactive agent is infused into the patient's body and ideally, should be absorbed only into the diseased cells at a treatment site that are to be destroyed by the therapy. A photoreactive agent has a characteristic light absorption waveband and reacts when exposed to light within that waveband by destroying any cells that have absorbed it. When a light source producing light having the absorption waveband of a particular photoreactive agent is directed at a treatment site at which cells have preferentially absorbed the agent, those cells will be destroyed by the photodynamic reaction. It is clearly preferable that the exposure of healthy tissue to the photoreactive agent be limited, so that the exposure is confined to diseased tissue within the internal treatment site, e.g., within a tumor. Even if the photoreactive agent is injected directly into a treatment site, some of the photoreactive agent may be carried away from the treatment site, and its toxicity may adversely affect healthy tissue and thus, impact on the health of the patient. Clearly, it would be preferable to target the photoreactive agent within the treatment site and minimize the risk of the substance being carried outside the treatment site by bodily fluids.

Researchers have developed both passive and active drug targeting techniques for concentrating therapeutic drugs at particular treatment sites within the body. Two well-known passive drug targeting techniques for the distribution of therapeutic drugs to diseased portions of the body are referred to by the terms "antigen directed" and "liposome encapsulated," respectively. The antigen directed technique is typically employed to bind antibodies to therapeutic substances, such as anticancer drugs or immunotoxins. This substance with the bound antibodies is injected into the patient's body, so that a significant amount of the antibodies are carried by the patient's circulatory system to diseased tissue throughout the body, where the antibodies concentrate the therapeutic substance. The liposome encapsulated technique coats a therapeutic drug with another drug that is known to collect in a particular organ of the body, such as in the liver or the spleen. After the coated therapeutic drug is injected into the patient's body, a certain substantial percentage of the drug collects in the particular organ that is targeted for treatment. Thus, passive drug targeting techniques employ the body's natural processes to concentrate therapeutic drugs at particular treatment sites within the body.

In contrast, active drug targeting techniques do not rely as much upon the body's natural processes to concentrate a therapeutic drug in a particular portion of the body. Instead, external forces are used to achieve this goal. For example, a medical practitioner can direct a strong external force, such as a magnetic field, at a treatment site in order to attract a magnetic fluid that includes a therapeutic drug. In the prior art, there are two types of magnetic fluids employed for active drug targeting. The first type combines a therapeutic drug with a plurality of metallic particles that are suspended in an aqueous solution, such as saline, to create a magnetic fluid. The second type of magnetic fluid employs metallic magnetically attracted particles that are coated with a polymeric material. The polymeric coating is selected for its ability to bind a therapeutic drug directly to the magnetic particles by adsorption, which is reversible. The coated and bound metallic particles are suspended in a solution, such as saline. When either type of magnetic fluid is injected into the patient's body, it is attracted by the strong magnetic field to the treatment site, thereby concentrating the therapeutic drug at that site.

In the prior art, strong magnetic fields have been directed to a treatment site using electromagnetic coils that are disposed outside of the patient's body. However, there are several inherent problems in using an externally positioned magnetic field generator such as an electromagnet. First, the patient is not ambulatory during the treatment, because the patient must remain motionless in close proximity to the external magnetic field generator while the magnetic fluid carrying the drug is infused, so that the therapeutic substance can be thus concentrated at the treatment site. The size and weight of a typical magnetic field generator capable of producing a magnetic field large enough to attract the magnetic fluid to the treatment site and the need to be coupled to a relatively powerful power source to energize the magnetic field generator precludes a patient from easily carrying the generator about while the desired concentrating action of the magnetic flux occurs. Second, it is extremely difficult to narrowly focus an externally produced magnetic field on diseased tissue that is disposed deep within a patient's body. The deeper within the body that an externally generated magnetic field must extend to reach a treatment site, the greater the amount of healthy tissue that will also be exposed to the magnetic field. Since magnetic fluids are attracted to strong magnet fields, the fluid tends to collect in any tissue where such a field exists. Finally, studies have shown that strong magnetic fields can have a deleterious effect on human tissue by increasing the rate at which free radicals are created in cells; free radicals can damage the cells. Thus, there is a need to provide an implantable magnetic source that can produce a magnetic field at a treatment site within diseased tissue, while limiting the overall exposure of healthy tissue to the magnetic field. In this way, a magnetic fluid that includes a therapeutic drug can be selectively targeted and concentrated in a treatment site within a particular portion of the patient's body, without causing adverse effects to other tissue.

SUMMARY OF THE INVENTION

In accord with the present invention, a method for concentrating a medicinal substance at an internal treatment site within a patient's body is defined and includes the steps of providing a magnet, and providing a fluid that is attracted to the magnet. The fluid includes the medicinal substance. The magnet is inserted through an opening into the body and advanced to the internal treatment site. Further, the fluid is supplied to the patient's body so as to encourage the fluid to be conveyed to the internal treatment site. The magnet attracts the fluid to provide a substantially increased concentration of the medicinal substance at the internal treatment site, relative to surrounding tissue. The fluid comprises metal particles that are attracted to a magnetic field.

While not necessary, the method may include the step of removing the magnet from the patient's body after the desired therapy has been provided.

In one embodiment of the invention, a plurality of magnets are inserted and disposed at spaced apart points within the internal treatment site. Preferably, each magnet is sealed within a biologically inert material. Also, in one form of the invention, the magnet comprises a rare earth metal. Alternatively, the magnet may comprise an electromagnet that is adapted to be coupled to and energized by current provided by a power supply inside or outside the body. If an electromagnet is used, the electrical current can be selectively varied to adjust a magnetic field intensity of the electromagnet. Regardless of the type used, the outer surface of the magnet (probe) may be coated with the medicinal substance.

In the disclosed preferred embodiment, the medicinal substance is preferably a photoreactive agent that is absorbed by tissue at the internal treatment site. In this case, the method further comprises the steps of providing a light source that is inserted into the patient's body and positioned at the internal treatment site, and a power supply for energizing the light source. The internal treatment site is then illuminated with light emitted by the light source so that the photoreactive agent absorbed by the tissue is activated by the light source to provide the PDT.

In one technique, the step of supplying the fluid preferably comprises the step of infusing the fluid into a blood vessel upstream of the internal treatment site so that the fluid is carried through the blood vessel into the internal treatment site.

A further aspect of the present invention is directed to a system for concentrating a medicinal substance at an internal treatment site within a patient's body. The system includes components that are generally consistent in function with the steps of the method discussed above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 5 is a cross-sectional view of the PDT probe and a pair of magnetic probes disposed in a tumor;

FIG. 6 is a cross-sectional view of a magnetic probe taken along section lines 6—6 in FIG. 5;

FIG. 8 is a side view of the PDT probe disposed inside a patient's body, directly adjacent to a tumor within the stomach wall, and showing a spherical magnetic probe that is disposed adjacent to the tumor, within the stomach;

FIG. 9 is a cross-sectional view of the magnetic probe taken along section lines 9—9 in FIG. 8;

FIG. 10 is a side cross-sectional view of another embodiment of the PDT probe and a pair of electromagnetic probes in a tumor;

FIG. 11 is a cross-sectional view of the electromagnetic probe taken along section lines 11—11 in FIG. 10;

FIG. 12 is a cross-sectional view of the embodiment of the PDT probe depicted in FIG. 10, taken along section lines 12—12;

FIG. 13 is a cross-sectional view of the embodiment of PDT probe shown in FIG. 10, taken along section lines 13—13;

FIG. 14 is an end view of the embodiment of the PDT probe taken along section lines 14—14 in FIG. 10;

DESCRIPTION OF THE PREFERRED EMBODIMENT

Magnetic fields are generated using either electromagnets or permanent magnets. An electromagnet has a core that is encircled by a winding comprising an electrical conductor coiled in a plurality of loops. The electromagnet is energized with an electrical current supplied by a power source that is electrically coupled to the winding. In an electromagnet, the magnitude and the period of the magnetic field are determined in part by the magnitude and period of electrical current flowing through the windings. In contrast, a permanent magnet provides a constant magnetic field and need not be coupled to a power supply, since it does not require any electrical current.

Recently, a new type of permanent magnetic material has been developed, which generates a magnetic field 5 to 10 times greater than a conventional alnico permanent magnet per unit of weight. These new magnets are fabricated of rare earth metals, such as neodymium, and they can be manufactured in a wide variety of shapes. Additionally, rare earth magnets can have physical dimensions smaller than an electromagnet or conventional alnico magnet that produces an equivalent magnetic flux density.

In the present invention, super neodymium (or other rare earth) permanent magnets having biocompatible coatings are preferably employed as implantable magnetic field generators that are disposed adjacent diseased tissue at a treatment site. Because the magnets are placed at or within a treatment site, the magnetic field in the surrounding healthy tissue is minimized. These magnets generate a substantial magnetic field at the treatment site that attracts a magnetic fluid including at least one therapeutic or medicinal substance. The preferred embodiment of the present invention disclosed below is specifically used for increasing the concentration of a photoreactive agent at a treatment site for use in administering PDT to the site; however, it should be apparent that the present invention can alternatively be used to increase the concentration of a different type of medicinal substance at an internal treatment site for use in administering a different type of medical therapy to the site.

Figure 1:
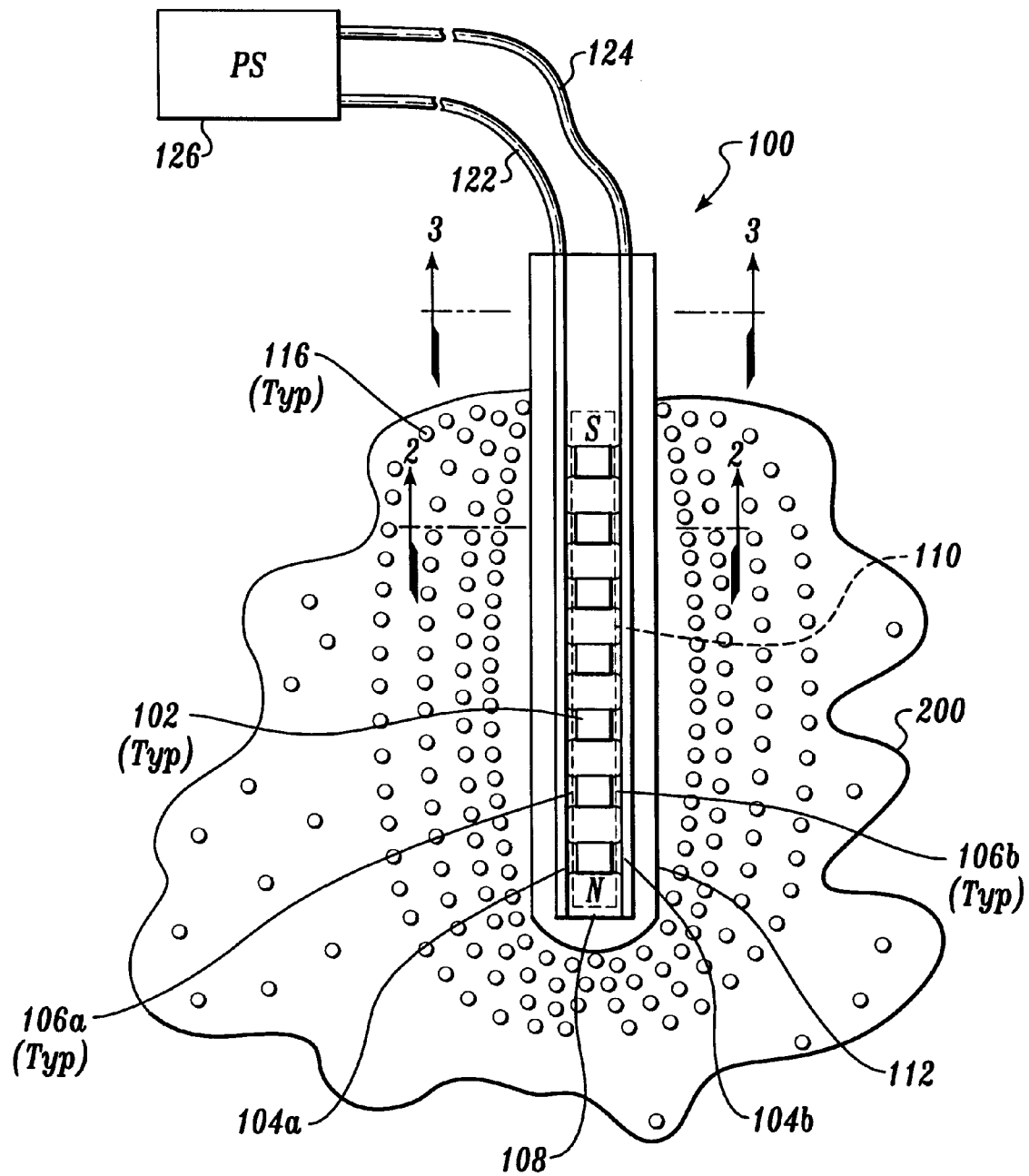
FIG. 1 is a side cross-sectional view of a PDT probe disposed in a tumor having a plurality of magnetic particles in close proximity to the probe due to a magnetic flux produced by a magnet within the PDT probe.

In FIG. 1, a PDT probe 100 is positioned at a tumor 200, which is disposed within a patient's body. A plurality of light emitting devices (LEDs) 102 are coupled to a pair of conductive traces 104a and 104b, along opposite sides of a support 108. Alternatively, other types of light sources, such as laser diodes, fluorescent devices, electroluminescent device, or gas discharge devices can be employed as light sources instead of LEDs. LEDs 102 are arranged in a substantially linear and evenly spaced array along the portion of the probe that is disposed within tumor 200. A power supply 126 is coupled through a pair of leads 122 and 124 to conductive traces 104a and 104b. The conductive traces are energized with an electrical current from power supply 126. The electrical current causes the LEDs to emit light so that PDT can be administered to the treatment site. A sheath 112 fully envelops the probe and is formed of an optically transparent and biologically inert material. Only one surface of support 108 is visible in the Figure, but the opposite side is identical, including additional LEDs mounted thereon.

In administering PDT, the treatment site is normally infused with an appropriate photoreactive agent, which is spread throughout the tissue surrounding the site, but is preferentially absorbed by the abnormal cells that are to be destroyed by the PDT. However, as noted above in the Background of the Invention, the photoreactive agent can be cytotoxic, possibly harming normal tissue as the agent is carried by blood and other fluids throughout the patient's body. The present invention avoids this problem by binding the photoreactive agent to particles that are attracted to a magnet. The particles, with the photoreactive agent bound thereto, are delivered as a fluid to the treatment site. In the following discussion, these particles are referred to as "magnetic particles"—not to indicate that they are permanent magnets, but instead to indicate that they are attracted by a magnetic field. However, it is also contemplated that either metallic or non-metallic (e.g., ceramic) permanent magnetic materials can alternatively be used for magnetic particles 116. Ceramic magnetic particles will have the advantage of being biologically inert.

As shown in FIG. 1, a plurality of magnetic particles 116 are inhomogeneously distributed throughout tumor 200, with the highest concentration of the particles being evident immediately adjacent to sheath 112 of a PDT probe 100. In the preferred embodiments discussed below, the magnetic fluid is preferably of the type in which the photoreactive agent or other therapeutic agent or drug is bound to a polymeric coating that encapsulates magnetic particles in a fluid suspension. It will be apparent that where the magnetic particles are more heavily concentrated, the photoreactive agent bound to the magnetic particles is also highly concentrated. Furthermore, because the magnetic particles are attracted to a magnetic field, they and the photoreactive agent (or other therapeutic drug) that is bound to them are much less likely to be carried away from the treatment site to other parts of the patient's body than if the photoreactive agent were simply infused into the patient's body in the conventional manner. Instead, the photoreactive agent bound to the magnetic particles will be preferentially absorbed by abnormal tissue or undesirable organisms at the treatment site for subsequent activation by light of a waveband corresponding to the absorption waveband of the photoreactive agent. The PDT subsequently administered should destroy the abnormal tissue or undesired organisms at the treatment site.

Figure 2:
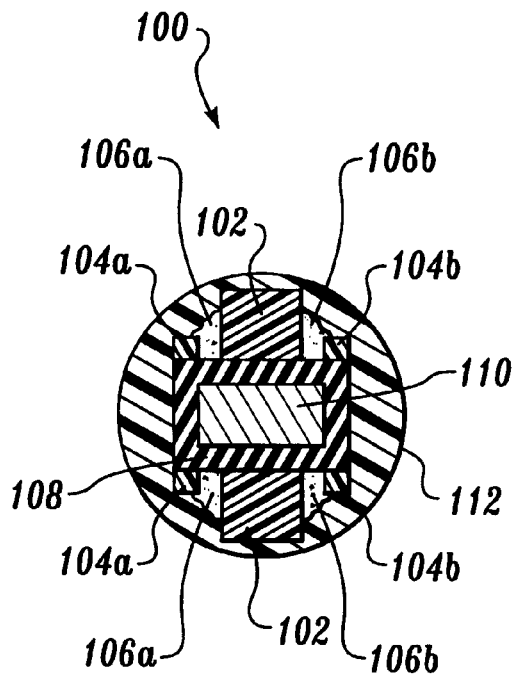
FIG. 2 is a cross-sectional view of the PDT probe taken along section lines 2—2 in FIG. 1 and showing a pair of light sources coupled to a pair of conductive traces and attached to a support that has a magnetic core along the centerline of the longitudinal axis of the probe.
Figure 3:
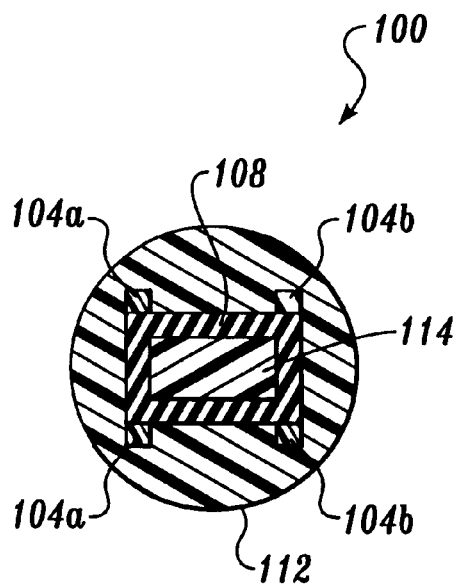
FIG. 3 is a cross-sectional view of the PDT probe taken along section lines 3—3 in FIG. 1.

As indicated by the dashed line in FIG. 1 and in the cross-sectional view of the PDT probe provided in FIGS. 2 and 3, an elongate permanent magnet 110 of neodymium alloy and having a rectangular cross section is disposed along the centerline of the longitudinal axis of that portion of PDT probe 100, which is disposed within tumor 200. Magnet 110 is encapsulated in a support 108, and the support also has a cross section that is rectangular in shape, with a center cavity 114 that is shaped to conform to the outer surface of magnet 110. Further, support 108 is an electrically insulating material such as rubber. Alternatively, a coating of an electrically insulating polymer may be applied to the magnet. A plurality of LEDs 102 are arranged in spaced-apart linear array along the longitudinal axis of PDT probe 100, facing outwardly and on opposite sides of support 108. Two pairs of conductive traces 104a and 104b are also disposed on opposite sides of the support. Each pair of traces 104a and 104b are coupled to opposing terminals of each LED 102 on the same side of support 108, by a pair of conductive adhesive drops 106a and 106b, respectively. Although sheath 112 has a substantially circular cross section, its interior surface fully encapsulates and conforms to the shape of LEDs 102, traces 104a and 104b, adhesive drops 106a and 106b, support 108, and magnet 110. Sheath 112 extends along the entire length of PDT probe 100, its outer surface defining the substantially cylindrical shape of the PDT probe. The sheath comprises a biocompatible, optically transparent polymer.

Referring to FIG. 3, it will be noted that magnet 110 does not extend into cavity 114 in the proximal portion of probe 100 that is outside tumor 200. Instead, this portion of cavity 114 is filled with a biologically inert material such as polymer. By ensuring that the portion of the probe containing the magnet is completely within the treatment site, the maximum strength of the magnetic field created by magnet 110 is generally confined to tumor 200.

Figure 4:
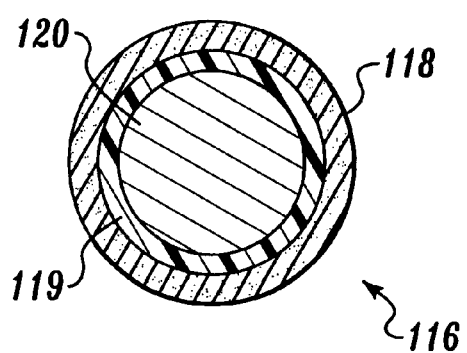
FIG. 4 is a cross-sectional view of a magnetic particle.

In FIG. 4, one of the magnetic particles 116 is shown. In the schematic view, the magnetic particle has a core 120 which is circular in cross sectional area, but it should be noted that the magnetic particles can be any regular or irregular shape. As noted above, the magnetic particles preferably comprise a material that is attracted to magnetic fields, such as a ferrous or rare earth metal or alloy. Magnetic particle 116 is encapsulated by a polymeric coating 118 that has adsorbed an appropriate photoreactive agent (or other medicinal substance). An inner biocompatible coating 119 of a polymer such as TEFLON™ encapsulates core 120 and serves as a barrier between the photoreactive agent coating and core 120. Further, coating 118 enables the binding of the photoreactive agent directly to magnetic particle 116, but reversibly, by adsorption. When the photoreactive agent that comprises coating 118 is absorbed by tissue, the inner biocompatible coating 119 of polymer that is then exposed will prevent the material that comprises the core from directly contacting the surrounding tissue. Although not shown, magnetic particle 116 may also be provided without polymeric coating 119, so that polymeric coating 118 that includes the medicinal substance coating may be applied directly to the surface of core 120.

Referring to FIG. 5, PDT probe 100 is disposed transversely across a middle portion of an elongate tumor 202. Further, a pair of rod-shaped magnetic probes 128a and 128b are disposed transversely across opposite ends of tumor 202. Each of these magnetic probes includes a magnet of super neodymium or another magnetic rare earth metal or alloy in its core 130, and the magnets in the two probes are oriented so that their magnetic poles are at opposite ends relative to their transverse disposition in the tumor. With this configuration, a strong magnetic field is established through the interior of tumor 202, between the two magnetic probes. A plurality of magnetic particles 116 are infused into tumor 202. Because of the magnetic flux between the two magnetic probes, the particles will be attracted to the portion of tumor 202 adjacent to probe 100 between magnetic probes 128a and 128b. Although not shown in the drawings, the magnetic flux density is greatest adjacent to the poles of the magnets, and thus, the particle concentration would tend to be greater adjacent to the magnetic poles. Fluid movement within the tumor may tend to distribute the particles away from the poles.

Looking at FIG. 6, core 130, which is disposed along the longitudinal axis of magnetic probes 128a/128b, is illustrated as having a substantially circular cross section. A sheath or coating 132 having a substantially circular cross section and comprising a biologically inert material fully encapsulates core 130. It is envisioned that sheath 132 can be TEFLON™ or another suitable polymer selected to ensure that the magnetic probe is biologically inert. Additionally, since tumors can have a variety of shapes, it is envisioned that a user would select a combination of PDT probes and magnetic probes from among various sizes and lengths to optimize the beneficial effects of PDT for a particular treatment site within a patient's body. Also, in those cases where PDT is not the desired form of therapy, the medical practitioner can employ implantable magnetic probes without the PDT probe, to attract a magnetic fluid that includes a suitable therapeutic agent or drug, thereby concentrating the therapeutic agent or drug in the diseased tissue at the treatment site.

Figure 7:
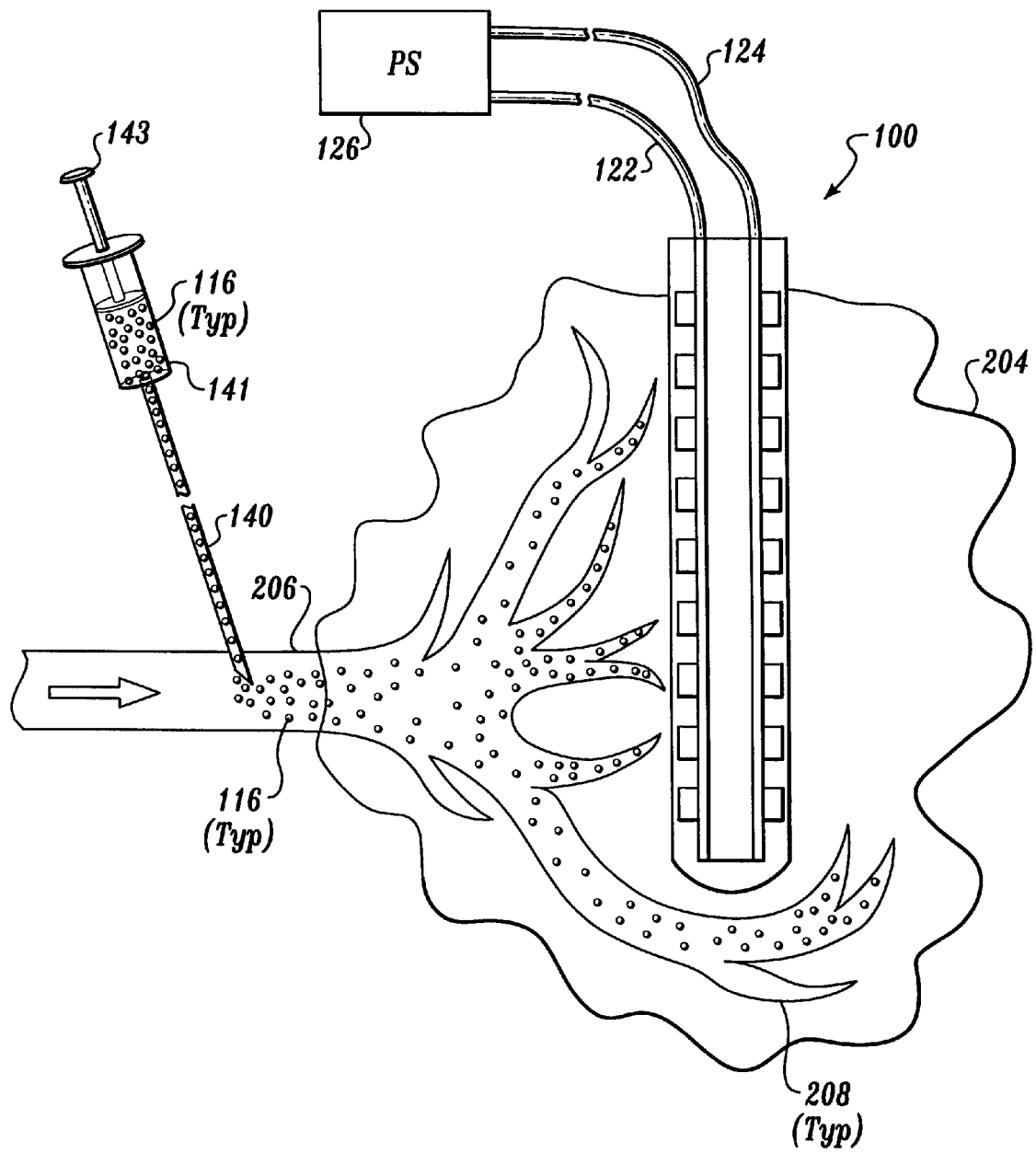
FIG. 7 is a cross-sectional view of the PDT probe disposed in a tumor illustrating magnetic particles being injected into a blood vessel that supplies the tumor.

In FIG. 7, PDT probe 100 is shown disposed within a tumor 204 that receives its blood supply through an artery 206 and a plurality of capillary blood vessels 208. A hypodermic needle 140 is inserted into artery 206, so that pressure applied to a plunger 143 causes a plurality of magnetic particles 116 suspended in a fluid such as a biological saline solution to be forced from a syringe body 141 into blood vessel 206. Particles 116 in artery 206 travel into those portions of capillary blood vessels 208 that are in close proximity to PDT probe 100 and are thus infused into the treatment site. The magnetic particles tend to concentrate around PDT probe 100 due to their attraction to the magnetic field of the magnet included within the probe. The photoreactive agent carried by the magnetic particles is absorbed into the malignant cells of the tumor, forming a relatively high concentration of the photoreactive agent in the malignant cells around PDT probe 100. An electrical current is provided by power supply 126 through leads 122 and 124 to probe 100, so that PDT can be applied to those portions of tumor 204 and the malignant or abnormal cells that have absorbed the photoreactive agent are destroyed by the photodynamic reaction caused by the light emitted from the PDT probe.

Turning now to FIG. 8, a tumor 212 is disposed at the pyloric zone within the wall of a stomach 210. A magnetic probe 134 having a substantially spherical shape is positioned inside of stomach 210 in proximity to tumor 212. PDT probe 100 is disposed within the abdominal cavity of the patient, directly below stomach 210 and adjacent to tumor 212. Magnetic particles 116 have been infused into tumor 212. It is envisioned that the magnetic fields created by PDT probe 100 and magnetic probe 134 would preferably be orientated in opposite polarity, i.e., to provide for mutual attraction, as shown in the Figure. In this configuration, the magnetic field passing through tumor 212 is intensified and the possibility of an inadvertent displacement of either PDT probe 100 or magnetic probe 134 from the treatment site is minimized. Although not shown in the Figures, it is further envisioned that the relative location of PDT probe 100 and magnetic probe 134 could be reversed. In this case, PDT probe 100 would be disposed inside stomach 210 and magnetic probe 134 would be disposed outside of the stomach and directly adjacent to the tumor receiving PDT. Probe 100 would be coupled to power supply 126 (located outside the patient's body) by conductors 122 and 124, which would pass from the power supply, through the patient's esophagus, and into stomach 210, enabling the PDT probe to be positioned in close proximity to tumor 212.

In FIG. 9, details of magnetic probe 134 include a spherically shaped core 138; the core is fabricated of a permanently magnetic material such as super neodymium alloy and is encapsulated within a shell or coating 136 that is a biologically inert material such as a TEFLON™ polymer.

In the above-disclosed preferred embodiments, all of the permanent magnets are formed of a rare earth metal or alloy having a magnetic field substantially greater than a conventional alnico magnet per unit of weight. However, an electromagnet could alternatively be included in a probe that is inserted into a treatment site to attract magnetic particles that carry a medicinal substance. For example, as shown in FIGS. 10 and 11, a PDT probe 100' is disposed transversely across a middle portion of an elongate tumor 202. Further, a pair of cylindrical magnetic probes 142a and 142b are disposed transversely across the opposite ends of tumor 202 so that PDT probe 100' is disposed about midway between the two magnetic probes. Each magnetic probe includes an electromagnetic winding 150 around a core 152 of soft iron or other ferrous alloy, which extends along the longitudinal axis of the magnetic probe. Windings 150 in the two magnetic probes are connected so that the electrical current flows through the windings in each probe in opposite directions. As a result, the magnetic poles of the magnetic probes are opposite in polarity. Thus, as shown in FIG. 10, the south pole of electromagnetic probe 142a is at the top of the magnetic probe, while in electromagnetic probe 142b, the north pole is at the top.

Electrical current flowing from a current control 144 is conveyed to the electromagnets within probes 142a and 142b, respectively, by pairs of leads 146a and 146b, and 148a and 148b. A strong magnetic field can be established through the interior portion of tumor 202, between the two magnetic probes when electrical current is flowing through windings 150 in the electromagnets. A sheath or coating 154 comprising a biologically inert material, such as a TEFLON™ polymer, fully encapsulates core 152 and winding 150 in each electromagnetic probe, and also is applied around leads 146a/148a and 146b/148b. Electrical current from power supply 126 is optionally applied to current control 144, so that the user can adjust the amount of current supplied to the electromagnets in probes 142a and 142b. While details of the remote control circuitry employed are not shown, the adjustment of the current level by current control 144 can be accomplished from outside a patient's body, enabling the current control and power supply 126 to be implanted within the patient's body. Alternatively, the power supply and current control may be externally disposed.

The employment of an electromagnet in a probe enables the user to optimize the intensity of the magnetic field at a particular treatment site for the attraction of a magnetic fluid that includes a desired therapeutic agent or drug to achieve the optimal concentration in the tissue of the tumor. In addition, the magnetic field can be selectively reduced or de-energized when the magnetic particles are being introduced into the organ through probe 100' as explained below.

PDT probe 100' does not include a permanently magnetic material or an electromagnet. Instead, the probe has an internal lumen 158 extending along its longitudinal axis that is connected by a fluid line 162 to a magnetic fluid supply 164. While illustrated as a separate block, magnetic fluid supply 164 is alternatively contained within a reservoir or cavity disposed within the proximal end (i.e., the upper end as shown in the Figure) of PDT probe 100'.

As shown more clearly in FIG. 12, a plurality of spaced-apart horizontally opposed ports 156a and 156b extend radially outward from lumen 158 from the longitudinal axis of PDT probe 100'. Referring to FIG. 14, a port 160 is also disposed at the distal tip of probe 100'. Since ports 160, 156a, and 156b all have relatively small diameters, the magnetic fluid in lumen 158 flows out through the ports at a relatively uniform rate. Magnetic particles 116 in the fluid contained within magnetic fluid supply 164 are conveyed through fluid line 162 and into lumen 158, infusing into tumor 202 through port 160 and plurality of ports 156a and 156b. The magnetic fluid is dispersed throughout tumor 202, but due to the lines of magnetic flux coupling the north and south poles of the two electromagnetic probes, a much higher concentration of the magnetic fluid occurs adjacent to PDT probe 100', along the magnetic flux lines extending between the opposite poles of electromagnetic probes 142a and 142b, and along the magnetic flux lines extending between the north and south poles of each electromagnetic probe.

As shown in FIG. 12, two pairs of conductive traces 104a and 104b are disposed on opposite sides of the probe for connecting to opposed electrical contacts on each LED 102 positioned along the same side of support 108 using solder or a conductive adhesive. This view also illustrates how cavity 114 is filled with a biologically inert polymer except where lumen 158 is disposed in the center. FIG. 13 shows that PDT probe 100' does not include ports 156a and 156b in the portion of the probe that is outside the tumor, i.e., its proximal end, thereby limiting the infusion of magnetic fluid to the interior of tumor 202. In this portion of the PDT probe, cavity 114 (without the polymer fill) may comprise the reservoir for magnetic fluid supply 164.

In an alternative embodiment (not shown) that does not use electromagnetic probes 142a and 142b, PDT probe 100' is fabricated with an electromagnet coil wound around a core. An internal lumen 158 extends through the center of the core, along the probe's longitudinal axis. In this embodiment, the PDT probe's electromagnetic coil would be de-energized while magnetic fluid is infused into the treatment site within tumor 202 through radial passages 156a and 156b, which extend through the windings of the coil. Thereafter, the electromagnetic coil would be energized with an electrical current from current control 144. The magnetic particles in the fluid infused into the tumor would then be attracted to the magnetic field, maintaining an increased density of the magnetic particles and of the photoreactive agent that they carry, around the probe to enhance the efficacy of the PDT.

The magnetic fluid carrying the photoreactive agent or other therapeutic agent or drug can be infused through a lumen in a catheter optionally coupled to lumen 158 in the PDT probe or inserted into the patient's body so that the distal end of the catheter and an opening from the lumen running through the catheter is disposed adjacent to the PDT probe, or at least within the treatment site. It is also contemplated that a magnetic probe can be left in place at the treatment site after the therapy had been completed, since the magnetic probe should not adversely affect the patient due to its biologically inert envelope or coating. Further, it is envisioned that a magnetic probe could be coated with the therapeutic agent or drug to further enhance the absorption of the therapeutic agent by cells or tissue surrounding the probe, at the treatment site.

Figure 15:
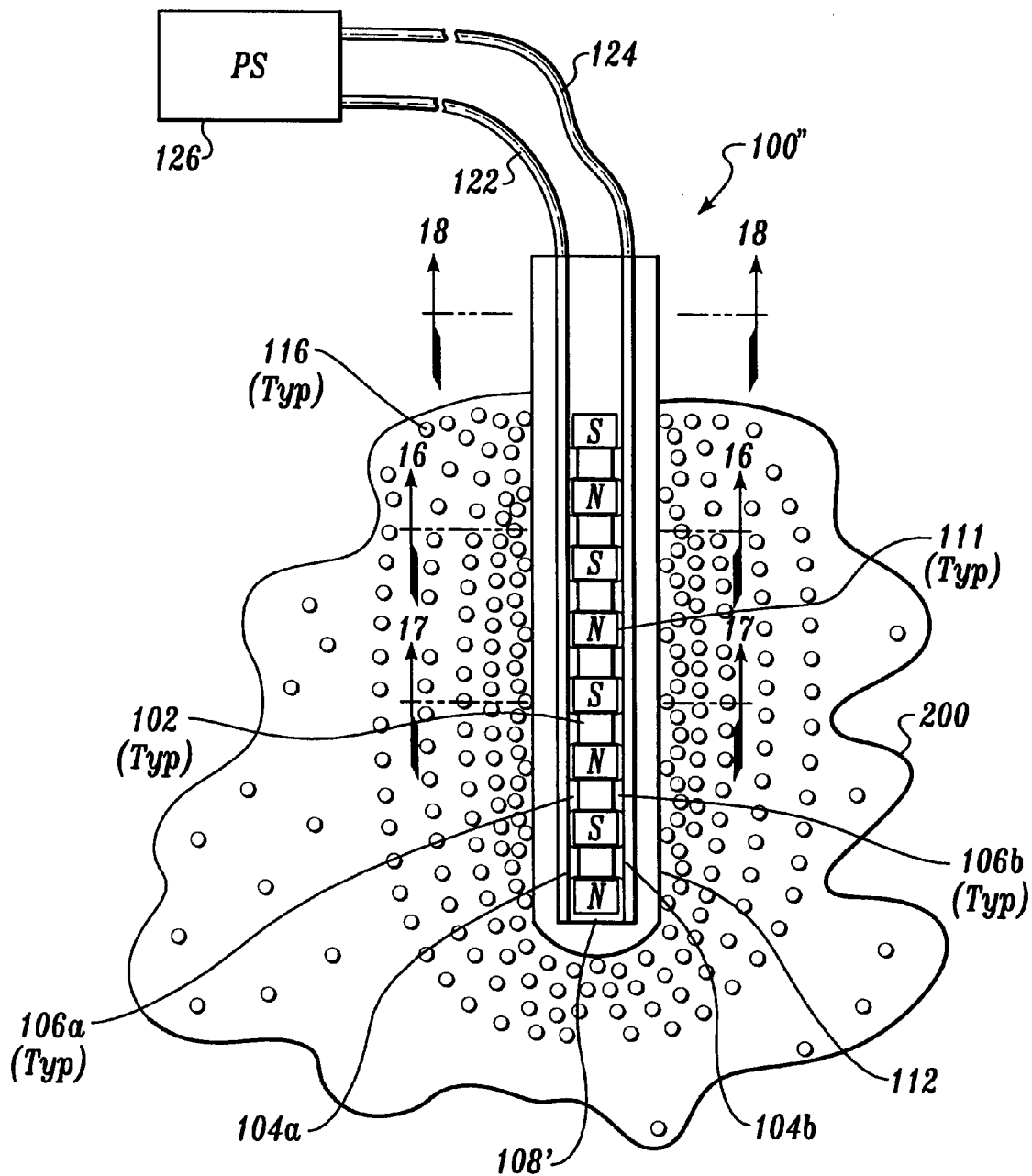
FIG. 15 is a side cross-sectional view of another embodiment of the PDT probe disposed in a tumor having a plurality of magnetic particles in close proximity to the probe due to a magnetic flux produced by a plurality of magnets transversely disposed within the PDT probe.

In all of the above-disclosed preferred embodiments, a single magnet is disposed along the longitudinal axis of the probe. However, a plurality of smaller magnets can alternatively be disposed transversely along the longitudinal axis of a probe that is inserted into a treatment site to attract magnetic particles that carry a medicinal substance. For example, as shown in FIG. 15, a PDT probe 100" is disposed at a treatment site within (or adjacent to) tumor 200. PDT probe 100" has a plurality of permanent magnets 111 disposed transversely along the probe's longitudinal axis in a spaced-apart array. Magnets 111 are interspersed with a plurality of LEDs 102, along the longitudinal axis of probe 100". Further, magnets 111 are positioned so that the north and south pole orientation for adjacent magnets alternates along the longitudinal axis of probe 100". In this way, the magnetic field flux density between the north and south poles for each successive pair of magnets 111 is concentrated directly adjacent to the particular LED 102 that is disposed between the pair of magnets. Moreover, magnetic particles 116 are preferentially attracted to the highest magnetic flux density extending outside the probe. Consequently, a plurality of magnetic particles 116 are inhomogeneously distributed throughout tumor 200, with the highest concentration of the magnetic particles occurring along the length of sheath 112, in the portion of tumor 200 that overlies LEDs 102. Thus, the light emitted by LEDs 102 will provide PDT to the abnormal tissue surrounding the probe that has absorbed the photoreactive agent carried by the magnetic particles concentrated in that region.

Figure 17:
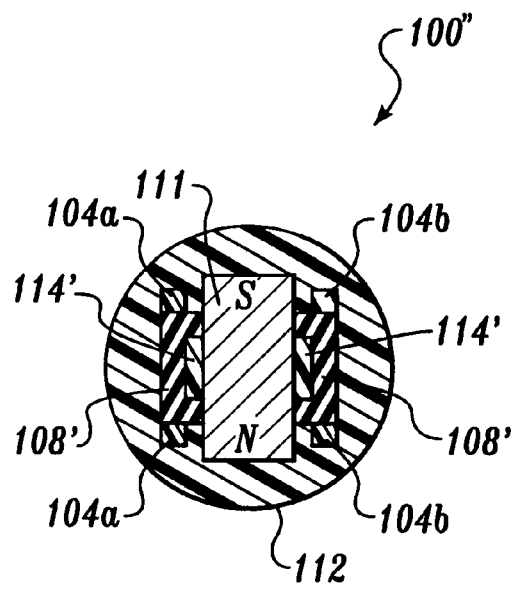
FIG. 17 is a cross-sectional view of the PDT probe taken along section lines 17—17 in FIG. 15 and illustrating two pairs of conductive traces attached to a support that has a magnetic core transversely disposed across the longitudinal axis of the probe.

In the cross-sectional view provided in FIG. 17, it can be seen that each permanent magnet 111 has a rectangular cross section and is disposed transversely along the centerline of the longitudinal axis of PDT probe 100". Each magnet 111 is mounted in an electrically insulative support 108', and the support also has a cross section that is rectangular in shape, with a center cavity 114' that conforms around the sides of magnets 111. The portion of cavity 114' that is not filled by magnets 111 is filled with a biologically inert material, such as polymer. Further, permanent magnets 111 comprise a rare earth metal or alloy having a magnetic field substantially greater than a conventional alnico magnet per unit of weight. Optionally, a coating of an electrically insulating polymer may be applied to magnet 111.

Figure 16:
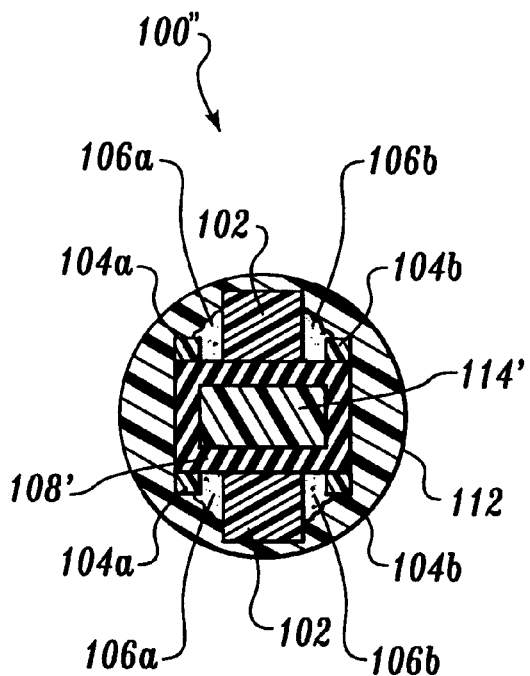
FIG. 16 is a cross-sectional view of the PDT probe taken along section lines 16—16 in FIG. 15 and showing a pair of light sources coupled to a pair of conductive traces and attached to a support.

In the cross sectional view of FIG. 16, a plurality of LEDs 102 are arranged in a spaced-apart linear array along the longitudinal axis of PDT probe 100, facing outwardly and on opposite sides of support 108'. Two pairs of conductive traces 104*a* and 104*b* are also disposed on opposite sides of support 108'. Each pair of traces 104*a* and 104*b* are coupled to opposing terminals of each LED 102 on the same side of support 108', by a pair of conductive adhesive drops 106*a* and 106*b*, respectively. Although sheath 112 has a substantially circular cross section, its interior surface fully encapsulates and conforms to the shape of LEDs 102, traces 104*a* and 104*b*, adhesive drops 106*a* and 106*b*, and support 108'. Sheath 112 extends along the entire length of PDT probe 100", its outer surface defining the substantially cylindrical shape of the PDT probe. The sheath comprises a biocompatible, optically transparent polymer.

Figure 18:
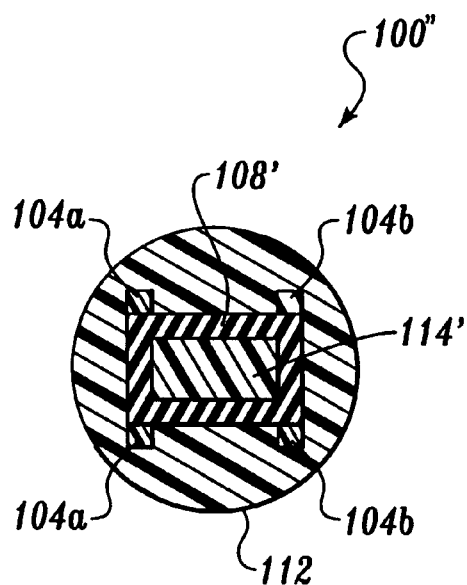
FIG. 18 is a cross-sectional view of the PDT probe taken along section lines 18—18 in FIG. 15.

Referring to the cross sectional view of FIG. 18, it will be noted that magnets 111 are not disposed in cavity 114' within the proximal portion of probe 100" that is outside of tumor 200. Instead, this portion of cavity 114' is filled with a biologically inert material such as polymer. By ensuring that the portion of the probe containing the magnets is completely within the treatment site, the maximum strength of the magnetic fields created by magnets 111 is generally confined to tumor 200, thereby ensuring that the magnetic particles and the photoreactive agent carried thereby are also generally confined to the tumor.

Although the present invention has been described in connection with several preferred forms of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for concentrating a medicinal substance at an internal treatment site within a patient's body, comprising the steps of:

(a) providing a magnet;

(b) providing a fluid that is attracted to the magnet and includes the medicinal substance;

(c) transcutaneously inserting the magnet through an opening made into the body and advancing said magnet to the internal treatment site; and (d) supplying the fluid to the patient's body so as to encourage the fluid to be conveyed to the internal treatment site, said fluid being attracted to the magnet to provide a substantially increased concentration of the medicinal substance at the internal treatment site, relative to surrounding tissue.

2. The method of claim 1, further comprising the step of removing said magnet from the patient's body.

3. The method of claim 1, wherein the step of inserting the magnet further comprises the step of inserting a plurality of magnets at spaced-apart points within the treatment site.

4. The method of claim 1, wherein the step of providing the magnet includes the step of providing a magnet that is sealed within a biologically inert material.

5. The method of claim 1, wherein the step of providing the fluid comprises the step of providing a fluid including one of a plurality of metallic non-magnetic particles, a plurality of metallic magnetic particles, a plurality of non-metallic magnetic particles, and a ferrous fluid.

6. The method of claim 1, wherein the step of providing the magnet includes the step of providing a magnet that comprises a rare earth metal.

7. The method of claim 1, wherein the step of providing the magnet includes the step of providing a magnet that is an electromagnet adapted to be coupled to and energized by current provided by a power supply.

8. The method of claim 7, further comprising the step of selectively varying the electrical current to adjust a magnetic field intensity of the electromagnet.

9. The method of claim 1, wherein the step of providing the magnet includes the step of providing a magnet that is coated with the medicinal substance.

10. The method of claim 1, further comprising the step of disposing the magnet adjacent to the internal treatment site.

11. The method of claim 1, wherein the step of supplying the fluid comprises the step of infusing the fluid into a blood vessel upstream of the internal treatment site so that the fluid is carried through the blood vessel into the internal treatment site.

12. The method of claim 1, wherein the medicinal substance is a photoreactive agent that is absorbed by tissue at the internal treatment site.

13. The method of claim 12, further comprising the steps of:

(a) providing a light source that is inserted into the patient's body and positioned at the internal treatment site;

(b) providing a power supply for energizing the light source; and (c) illuminating the internal treatment site with light emitted by the light source so that the photoreactive agent absorbed by the tissue is activated thereby, to provide a photodynamic therapy.

14. A system for concentrating a medicinal substance at an internal treatment site within a patient's body, comprising:

(a) a magnet;

(b) a fluid that is magnetically attracted to the magnet and includes the medicinal substance; and (c) means for transcutaneously inserting the magnet within the patient's body and for carrying the magnet to the internal treatment site, said magnet attracting the fluid so that the medicinal substance is concentrated within the internal treatment site.

15. The system of claim 14, further comprising a plurality of magnets that are dispersed in spaced-apart locations at the internal treatment site, a magnetic flux arising between the plurality of magnets causing the fluid to be concentrated in a region of the treatment site generally disposed between the plurality of magnets.

16. The system of claim 14, wherein the medicinal substance includes a photoreactive agent; further comprising a probe that is adapted to be inserted into the patient's body and employed to provide photodynamic therapy to tissue at the internal treatment site that has absorbed the photoreactive agent from the fluid.

17. The system of claim 16, wherein the probe includes a light source; further comprising a power supply for energizing the light source, so that the internal treatment site is illuminated with light emitted by the light source, said light activating the photoreactive agent to provide the photodynamic therapy to the internal treatment site.

18. The system of claim 16, further comprising a reservoir that stores the fluid, for delivery to the internal treatment site.

19. The system of claim 16, wherein the means for transcutaneously inserting comprises the probe, said magnet being disposed within the probe and carried thereby to the internal treatment site.

20. The system of claim 14, further comprising means for infusing the fluid into the treatment site.

21. The system of claim 20, wherein the means for infusing include a passage that conveys the fluid from a fluid supply to within the internal treatment site.

22. The system of claim 14, wherein the magnet is enclosed within a biologically inert material.

23. The system of claim 14, wherein the fluid comprises one of a plurality of non-magnetic metallic particles, a plurality of magnetic metallic particles, a plurality of non-metallic magnetic particles, and a ferrous fluid.

24. The system of claim 14, wherein the magnet comprises a rare earth metal.

25. The system of claim 14, wherein the magnet is an electromagnet, further comprising a power supply for providing an electrical current to energize the electromagnet.

26. The system of claim 25, further comprising a control for selectively varying a magnitude of the electrical current employed to energize the electromagnet, to change a magnetic field strength of the electromagnet.

27. The system of claim 14, wherein the magnet is coated with the medicinal substance.

28. The system of claim 14, wherein the medicinal substance is a photoreactive agent.

29. The system of claim 16, wherein the probe includes a plurality of magnets disposed therein, extending transversely across a longitudinal axis of the probe and having alternative north and south poles facing toward opposite sides of the probe.

30. The system of claim 14, wherein the fluid comprises ceramic magnetic particles that are substantially biologically inert.

* * * * *